(12) United States Patent
McBain

(10) Patent No.: US 9,993,183 B2
(45) Date of Patent: Jun. 12, 2018

(54) SYSTEM, METHOD AND DEVICE FOR CONFIRMATION OF AN OPERATOR'S HEALTH CONDITION AND ALIVE STATUS

(71) Applicant: Theodore Dean McBain, San Diego, CA (US)

(72) Inventor: Theodore Dean McBain, San Diego, CA (US)

(*) Notice: Subject to any disclaimer, the term of this patent is extended or adjusted under 35 U.S.C. 154(b) by 0 days. days.

(21) Appl. No.: 15/424,886

(22) Filed: Feb. 5, 2017

(65) Prior Publication Data
US 2017/0143241 A1 May 25, 2017

Related U.S. Application Data

(63) Continuation-in-part of application No. 13/340,673, filed on Dec. 30, 2011, now Pat. No. 9,878,802.
(Continued)

(51) Int. Cl.
*A61B 5/1171* (2016.01)
*G06K 9/00* (2006.01)
(Continued)

(52) U.S. Cl.
CPC .......... *A61B 5/1171* (2016.02); *A61B 3/0008* (2013.01); *B64D 45/0015* (2013.01); *G06F 21/32* (2013.01); *G06K 9/00201* (2013.01); *G06K 9/00604* (2013.01); *G06K 9/00617* (2013.01); *G06K 9/00892* (2013.01);
(Continued)

(58) Field of Classification Search
CPC ........................... A61B 5/1171; A61B 3/0008; G06K 9/00906; G06K 9/00604; G06K 9/00201; G06K 9/00617; G06K 9/00892; G06K 2009/00939
See application file for complete search history.

(56) References Cited

U.S. PATENT DOCUMENTS

2009/0253406 A1* 10/2009 Fitzgerald ............... G06F 21/88
455/410
2010/0278394 A1* 11/2010 Raguin ............. G06K 9/00604
382/117
2013/0278631 A1* 10/2013 Border ................. G02B 27/017
345/633

* cited by examiner

*Primary Examiner* — Ruiping Li
(74) *Attorney, Agent, or Firm* — Joshua Kaplan, Esq.; Kaplan Law Practice LLC

(57) ABSTRACT

An apparatus comprising a system with an array of sensors, sound and light emitting and receiving devices having at least one object control from a monitored object comprised of an operator, a patient, an animal, or machine, control of at least one performance parameter of the system; at least one iris/retina biometric sensor; at least one physiological iris/pupil sensor; at least one infinite random light emitter; said at least one iris/pupil biometric sensor; said at least one physiological pupil sensor and said one infinite random light emitter operatively connected and synchronized communication with each other utilizing at least one central processing unit; said at least one biometric sensor and said at least one physiological sensor delivering a parallel array of sensory readings to said central processing unit; said central processing unit capable of detecting a normal or an abnormal sensory reading; said at least one central processing unit capable of effecting said at least one performance parameter in response to said sensory reading; and said central processing unit recording said sensory reading on a storage medium to be used for identifying and detection of said alive status and health condition of the monitored object in real time.

20 Claims, 15 Drawing Sheets

Related U.S. Application Data

(60) Provisional application No. 62/388,683, filed on Feb. 5, 2016.

(51) Int. Cl.
 *A61B 3/00* (2006.01)
 *B64D 45/00* (2006.01)
 *G06F 21/32* (2013.01)

(52) U.S. Cl.
 CPC .... *G06K 9/00906* (2013.01); *B64D 2045/004* (2013.01); *B64D 2045/0055* (2013.01); *G06K 2009/00939* (2013.01)

64c

64d

64e

SYSTEM, METHOD AND DEVICE FOR CONFIRMATION OF AN OPERATOR'S HEALTH CONDITION AND ALIVE STATUS

CLAIM OF PRIORITY

This application claims priority of a previously filed United Stated Provisional Application No. 62/388,683, filed on Feb. 5, 2016, the contents of which are fully incorporated herein by reference. This application is a Continuation in Part of a co-pending U.S. patent application Ser. No. 13/340, 673, filed on Dec. 30, 2011, which is a Continuation in Part of a U.S. patent application Ser. No. 11/955,085, filed in Dec. 12, 2007, now issued as a U.S. Pat. No. 8,138,951, which is a continuation of the U.S. patent application Ser. No. 11/566,603, filed Dec. 4, 2006, which claims the benefit of U.S. patent application Ser. No. 10/251,666, filed Sep. 19, 2002, now issued as U.S. Pat. No. 7,145,477, and U.S. Provisional Application Ser. No. 60/323,754, filed Sep. 19, 2001, and expressly incorporates by reference the above-mentioned applications.

FIELD OF THE INVENTION

The present invention relates to authentication and data transfer systems based on unique biological and physiological attributes of objects or organisms being authenticated.

BACKGROUND OF THE INVENTION

In the world today, user identification through biometrics assumes, but cannot confirm, if an operator of a device is alive or not. Biometrics in the high tech world in which we live today are inheritably dangerous to the operator do to the fact that a criminal or terrorists may remove a person's eyeball, cut off a hand or finger and/or attempt to use various other methods of falsification to activate a device to gain access to data stored on a data storage device or gain controls for operation of device. This data can be bank accounts, healthcare and all other forms of information in which a company, governments or people need to keep private and prevent any unwanted persons from accessing the device data storage system.

Personal Identification

In the United States, a Social Security number (SSN) is a nine-digit number issued to U.S. citizens, permanent residents, and temporary (working) residents under section 205(c)2) of the Social Security Act, codified as 42 U.S.C. § 405(c)(2). The number is issued to an individual by the Social Security Administration, an independent agency of the United States government. Although its primary purpose is to track individuals for Social Security purposes, the Social Security number has become a de facto national identification number for taxation and other purposes. Social Security numbers were first issued by the Social Security Administration in November 1935 as part of the New Deal Social Security program. Within three months, 25 million numbers were issued. On Nov. 24, 1936, 1,074 of the nation's 45,000 post offices were designated "typing centers" to type up Social Security cards that were then sent to Washington, D.C. On Dec. 1, 1936, as part of the publicity campaign for the new program, Joseph L. Fay of the Social Security Administration selected a record from the top of the first stack of 1,000 records and announced that the first Social Security number in history was assigned to John David Sweeney, Jr., of New Rochelle, N.Y. Since the creation of the social security number, millions of individuals have had their identity stolen. There is a need for creating a hacker-proof system preventing future identity loses.

Truth Versus Falsehood

In the history of mankind, speaking words of untruth has been inherently problematic causing great harm and billions of lives have been effected throughout history. Vetting anyone at any time is what is needed for the betterment of global society. The ability to relieve the conscious, subconscious, and various other states of mind would be a major leap of the nature of humanity. This will allow the human mind to process thought without fear of any form to interfere with the process of thinking, thus enhancing and expanding the human brain and body. Minimizing stress on the human body, soul and spirit will take the level of life to elevated plateau for many years to come. Mankind might actually experience the Creator's wish of peace amongst ourselves and on Earth in our lifetime. Everyone gets a free pass from the past and a few for the future, but after that, penalties will ensue.

State of Health

Today's doctors have confirmed it is best to catch any health condition as soon as possible. Letting ailments go without treatment adds to the costs of healthcare and may lead to early death. Many people go long periods of time in between doctor visits and there are some that just hate going to see a doctor, period. What is needed is an ability to check and monitor the health status without having to go see a doctor or technician to determine when an operator/patient is in need of assistance. A device is needed with sensors creating an array of methods utilizing the sensors that feed data into a software system algorithm that will enable devices to determine various health conditions of the patient/operator. Also, doctors are overwhelmed by too many patient visits over limited time periods. If doctors had new tools for examining patients remotely they would be able to examine more patients in less time. Heal thyself has been desired since the early days of human existence and is the holy grail of the betterment of health and wellbeing, hence the desire to self-healing.

Internet of Things

Another critical environment of the internet of things (IOT) is the ability to hack into machines and compromise the integrity of the systems. These machines need to have their own identification solution similar to a human biometric signature. Without a new system and method of identifying machines, it will become extremely difficult to manage billions of devices in real time.

Also, in today's world the use of the binary code can be compromised relinquishing all data being transmitted. The high tech world of the IOT is in need of a safer, quicker and secure system for transferring data. Another problem in the communications industry is limited bandwidth for sending and receiving of data. A new system of protecting and compressing the data is a priority in the world of the IOT with billions of devices poised to be in everyday life. Today's world of terrorism, cyber and technology hackers, weapons of mass destruction and proliferation, economics and natural resource abuse, transnational organized crime, space and counter space, counter intelligence, human security, banking fraud, transportation security, personal information stolen, government asset protection, medical record storage facilities, hacking government personnel data, vetting immigrants correctly and accurately, medical records misused, stolen, lost, and hacked, home security, building security, internet fraud and abuse, hacking of internet of things, communication device security, transportation operations safety, corporate and industrial espionage, hospitals, nursing homes, rehab facilities, and the high costs of individual healthcare is needing a system and method for securing and lowering the cost of operations in the high tech world in which we live.

Many of our nation's most treasured achievements are at risk; national parks and monuments, roadway and infrastructure, industrial facilities, elderly care facilities are just a few of what is so dear to us and is in need of the greatest systems and methods of securing them without compromising privacy and freedom.

Various implements are known in the art, but fail to address all of the problems solved by the invention described herein. One embodiment of this invention is illustrated in the accompanying drawings and will be described in more detail herein below.

SUMMARY OF THE INVENTION

The main embodiment of the present invention incorporates several systems, methods, and devices for acknowledging the health condition, alive status, and identification of an operator/patient. The system operator activates a device and/or devices which then activates an array of sensors achieving a method of acknowledging the operator's true identification and health status. The device may also have various functions using sensors coupled with microphones, sound distribution system (external and internal), visual apparatuses, scent emitters and receivers, vibration apparatuses, all levels of light spectrum emitting devices, electronic needles and pressure distributions panels (medication delivery and acupuncture/acupressure) electro impulse emitters and brain analyzing sensors. By using one or more method and system for formulating healing, calming, soothing, pacemaker and/or artificial implants recharging/communicating systems, muscle activation system can be deployed to subconsciously, consciously and/or subliminally collect for use in attaining the necessary information for the desired level for healing or repairing malfunctioning systems. This can be achieved by infinite array of sounds (internal and external), visual effects, vibration effects, light transceivers and scent emitting sensory sensors and receivers. Scent receivers can be used to sense the scents given off by operators/patient/machines. The scent receivers can be used to identify and check health status of operators/patients/machines. The scent receiver's method of determining scents utilize systems similar to the Olfactory sensory system used in the nose of humans and animals. The olfactory epithelium contains special receptors that are sensitive to odor molecules that travel through the air. Lock and key method is the basic concept. The molecule has certain dimensions which only fit in to a special key receptor for that particular scent molecule, thus providing the necessary data needed to create a conclusion based on the data collected from one or many identification sensing systems. Machines containing scent molecular manufacturing abilities create infinite molecular crystal designs for use in communications of information and data. This system can be modified for use in private and secure methods of sending and receiving encrypted data and information by coding the molecules as data packets.

The "Alive Iris/pupil" method can be a simple function of a device emitting infinite random pulses of light and sound tracked by receiving device(s) i.e. camera(s), thermal camera(s), microphone, light absorbent material, laser light transceiver, scent receivers, LED or alike. Pupil expansion and contraction when synchronized with light impulses authenticates the operator as being alive and in real time. This may also check various health conditions by using the sensory sensing devices. The operator's iris and pupil are then set in motion by the random light pulses aimed at the operator's eyes, pupils, irises and facial features.

A retina and/or iris biometric signature scan is used in conjunction with the "Alive Iris/Pupil" checking system proving identity of the operator and health condition of operator/patient/machine. Since the infinite random light emitting device has an infinite light emitting ability, it then becomes impossible to use a video, dead eye or alike system and method to trick or compromise the security system. The security system incorporates a maximum amount of attempts before the security system for the data storage device shuts down the system. Information stored on communication device will then be uploaded to the cloud or some other storage system.

The technologies may be self-contained in the device and/or stored in various data storage devices. This system can be a simple application on a Smart Phone, tablet and/or any type of communication device used for identifying and authenticating the true operator of the device. The operator of the said device may allow other users with consent from the true owner of the device to use the device. It may also be able to communicate with emergency agencies and personal in the event of an emergency. This system may incorporate a pulsating laser for long distance authentication and identification purposes of an operator. The system may use light from surrounding light flashes and/or reflections of various objects in motion in the back ground of the operator to activate and authenticate the iris scanning system.

When this system is in use, the sensors acknowledges the activities of the objects in the back ground to make a determination of the activities against the movements of the operator's pupil and eye or aperture of an artificial operator eye and/or human eye. This system may also incorporate a random moving light source for motion detecting of the light source. The device may contain an individually designed crystal for device identification purposes. The design of the crystal may follow a frozen water crystal in the form of a snowflake configuration. These snowflake configurations are infinite in our universe. There are no two alike after a certain stage of development. This will be ideal for identifying machines and any form of an operator, whether human being, animal or artificially made device. This will provide machines with an individual crystal (biometric) identity. There may be one, two or more of the crystals made for individualized communications between the crystal transceiver devices for security purposes. This communication technique will allow for the manufacturers of the devices to have encrypted and restricted communications between the crystals transceiver devices enhancing security platforms on all levels.

Alive Biometric Signatures will create a simplistic accurate vetting and monitoring of individuals eliminating terrorists and terrorism. Alive Biometric Signatures secures internet portals, data servers, switching hubs and all communication devices eliminating cyber warfare & hacking. These systems when fully deployed and activated will be the end all solution for vetting of any individuals for all industries, private and public forums, courts and any other place where truth is a natural course. Alive iris is a simplistic method for accurately vetting and monitoring of individuals using any type of communication device. Elimination of lies will eradicate transnational organized crime, enhance counter intelligence abilities, save many lives potentially leading to potential world peace. Alive Iris/Pupil Scan Technology infuses an infinite random strobe light expanding and contracting the pupil in synchronization with Alive Pupil Tracker program and strobe light.

The "Alive Iris/Pupil" systems identifies individuals at high accuracy rate while delivering a series of health status reports. The system provides analyzation "live", "in real time" truth and lie detection analysis as well. This present invention analyzes the eye, pupil, iris, retina, eye lids, curvature of lens, eye, eye socket and surrounding area. "Alive Iris" can determine the following: Fear, anger, pain, love, drugs, alcohol, and lying from analyzing alterations in pupil size, speed and surrounding area. Dilated or constricted pupils provide knowledge of sympathy and hostility of individuals in real time. Pupil size reflects the state of body and mind.

The pupils react to emotional stimuli. Light activates pupil stimulation. The pupil reflex is involuntary and is one of the best methods of "Alive Status" determination. Skin Cancer, Cloudy Eye, Myasthenia Gravis, HIV/AIDS, Heart Attack, Stroke, Exophthalmos, Arcus Senilis, Homer's Syndrome, High blood pressure, Marfan's Syndrome, Hypertension, Head injuries, Metastatic cancer, Diabetes, Autoimmune disorders, High cholesterol, High triglycerides all can be determined by the eye and surrounding area.

The present invention uses one or numerous, sensors, software programs, transceiver devices, various systems and methods for detecting and analyzing the multitude of ailments. By using comparison analysis software driven algorithms in combination of communicating sensors enable the systems the abilities for preemptive diagnosis of the operator/patient/machine. Passive, active, and alive biometric data measuring services and devices will provide in real time the necessary data and information pertaining to the operator/patient state which enable the system to analyze the status and condition which then can provide the knowledge and system activation for determining potential cure or relief to the operator/patient/machine. These systems may incorporate one or several techniques for determining the condition of the operator/patient/animal/machine.

Smelling salts, Floral, citrus, tree and shrub/plant millings, and various spice scent cartridges along with scent mixing element inducing a wide variety of effects on the operator/patient/machine, thus allowing for in-depth analysis and/or cure for potential ailments or malfunctions. Every individual/civilization has their own unique scent and pheromones. These scents can be used for distinct characteristic differences between operators/patients/machines.

Artificial pheromones can be created using the lock and key method. These technologies must decentralize and fragment personal data into multiple storage methods and means providing the ultimate in privacy. Data is retained within unique algorithms utilizing numerous devices and storage methods and locations preventing unwanted loss of private and privileged data. This can be achieved by each operator/patient/animal/machine maintaining a percentage of personal data. When all segments connect with operator/patient/animal/machine and information on their person as in a wearable and/or implant device(s) may contain crystal(s) contained in bracelet, ring, bracelet, and/or wearable, wearable infused with implant devices preventing the data from being compromised. This may be achieved with one or several methods using a variety of algorithms, methods and devices created by using an array of sensors and devices for maintaining data privacy.

A further embodiment of the crystal technology would send crystal formations via photon and laser-light apparatus for receiving and sending of data. This can be used for sending information over long distances without cumbersome infrastructure. The data would be sent the speed of light.

Individual's all have unique Biometric Signatures which provide pinnacle solutions for safety, security and privacy. These technologies rely upon infused biometric sensors with an array of physiological sensors and devices for authentication and health status and/or system malfunctions of operators/patients/animal/machines. Those skilled in the art will now that this present invention has many other purposes beyond the scope contained here within this disclosure.

BRIEF DESCRIPTION OF THE DRAWINGS

FIG. 1 also demonstrates the authentication device's operation on an artificial eye.

DESCRIPTION OF THE PREFERRED EMBODIMENTS

Figure 1:
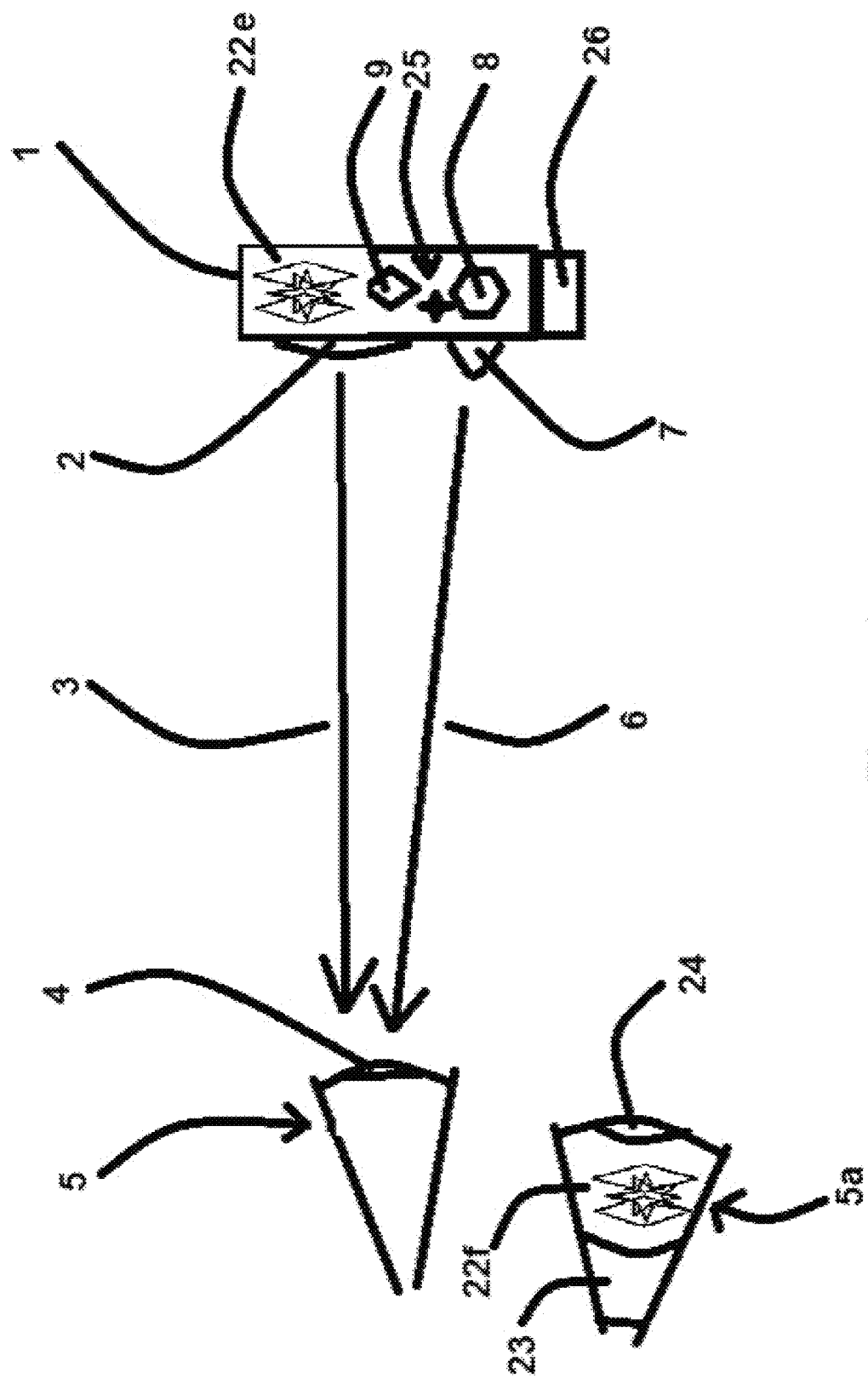
FIG. 1 is the preferred embodiment of the device that encompasses the authentication concepts described in the present invention.

The preferred embodiments of the present invention will now be described with reference to the drawings. Identical elements in the various figures are identified with the same reference numerals.

Reference will now be made in detail to embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

Turning now descriptively to the drawings, in which similar reference characters denote similar elements throughout the several views, the figures illustrate several embodiments of devices intended to authenticated objects or subjects being analyzed, and also are able to determine physiological and health qualities of the subject or object being monitored.

The above and other features and aspects of the present invention will become more apparent upon reading the following detailed information related in conjunction with the accompanying drawings in which are as follows: Shown in FIG. 1 is the communication device 1, which preferably carries on functions of identity authentication and health status of the operator device for one of the embodiments of the present invention. The communication device 1 contains the main control CPU 9, standard and thermal camera 2, light and sound emitting device 7, microphone 8. The light and sound emitting device 7 may use alternating levels and sequencing of light, time durations, proximity device ultrasonic sensing system. The purpose of utilizing alternating levels of light intensity and random light strobe emittances, is to ensure that the responses of the subject 5 or 5a are not prerecorded or falsified, but are actual, real time responses.

The ultrasonic system incorporates sound emitting device 7 with receivers offset from emitter allowing for three dimensional authentications 25. The proximity device 25 allows for the operator to be of distance from the communication device while recognizing the true operator for continuous operation. The offset is preferred to detect volume, as will be later described in FIG. 5. A volume of an object being authenticated is desired to ensure that the communication device 1 is not analyzing a screen or an immobile object, such as a detached eye. The camera is automatically directed 3 at the center of the operator eyeball. The light emitting device 7 automatically aims 6 the transmitted light at the operator's eyeball iris.

The communication device has a crystal 22e for machine identity (machine biometric signature). The communication device 1 utilizes iris scan technologies on the natural iris 5, which ensures authenticity by measuring reactions of the eye 5 to blinking lights or reflection of light emanating from light and sound emitting device 7. Another embodiment of the present invention is able to authenticate a machine or inanimate device 5a, an inanimate system 23 to be used on artificial intelligence aperture's 24. This device 5a may be identified and authenticated by the same process and means of the prior mention system and method of an operator of organic and artificial. The crystal 22f is used to authenticate the true identity of the operator. In a mechanical eye, or for that matter inanimate optical or communication equipment, authentication is performed by detecting light waves and light sequences emitted from or reflected by the object crystal 5a. Preferably the crystal 22e sends a light impulse through the light emitting device 7 to the object 5a. There these ultraviolet or visible light waves, or even photons, are detected by crystal 22f, and reflected back to the light wave sensitive visual detection device 2. Since in general, no crystal can be the same as any other, the light wave lengths or the type and frequency reflected by 22f will be unique to the particular object 5a. In this way, inanimate objects, such as consumer and professional electronic equipment, vehicles and communication media can be authenticated by the communication device 1.

The communication device 1 also has a transceiver 26. The transceiver 26 may use multiple forms of communicating methods. This method may incorporate multiple streams of communications simultaneously or singularly to achieve fragmentation of data being uploaded and downloaded. This can be achieved wirelessly using numerous methods including, but not limited to the following: Global positioning systems, ultrasonic sound systems, aqua vibrations systems, laser transceiver systems. The communication devices maybe hardwired using fiber optics and/or standard metallic forms. The multiple light emitting devices 7 transmits light at varying infinite intervals activating the receiving eyeball 5 iris 4 to increase or decrease in size dependent on the level and type of light being transmitted to the eyeball 5. The health status of the operator can be determined by using random light waves transmitted at the operator eyeball while the camera(s) are in synchronized with the light waves being transmitted.

Figure 2:
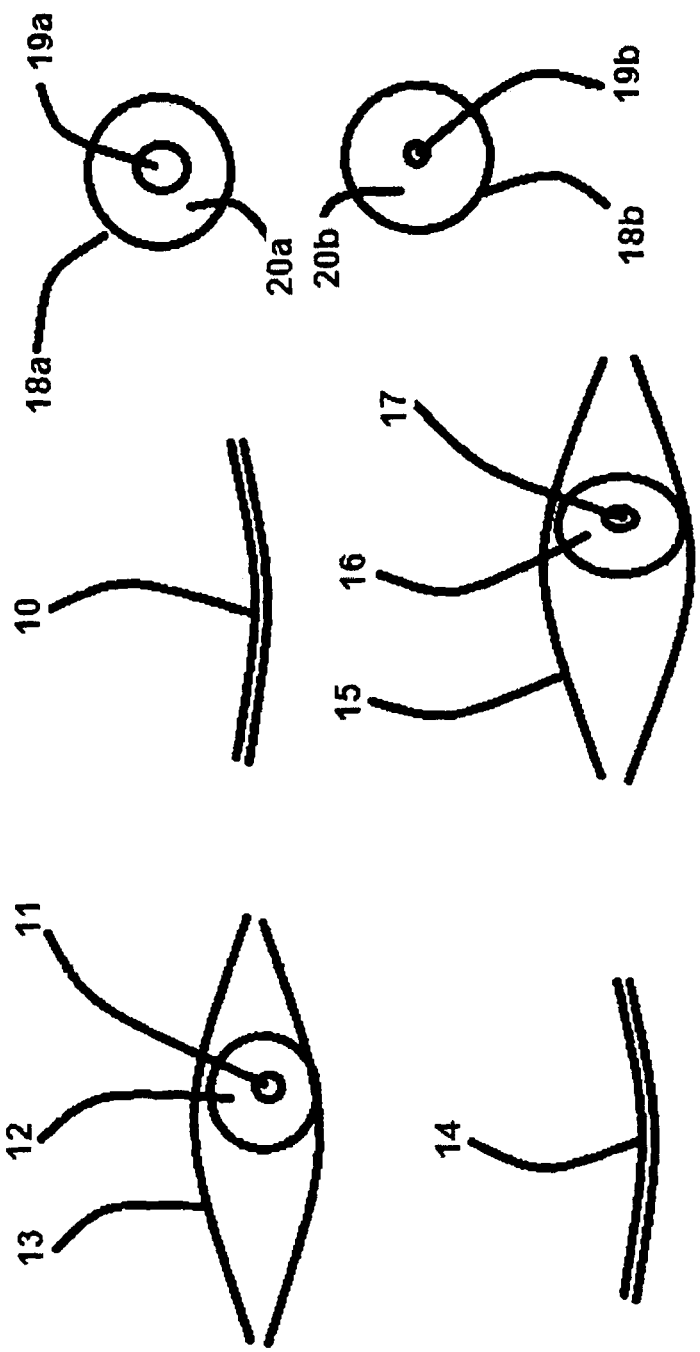
FIG. 2 is a diagram of the physiological attributes targeted by a device disclosed in FIG. 1, of a subject being authenticated using concepts disclosed in the present invention.
Figure 3:
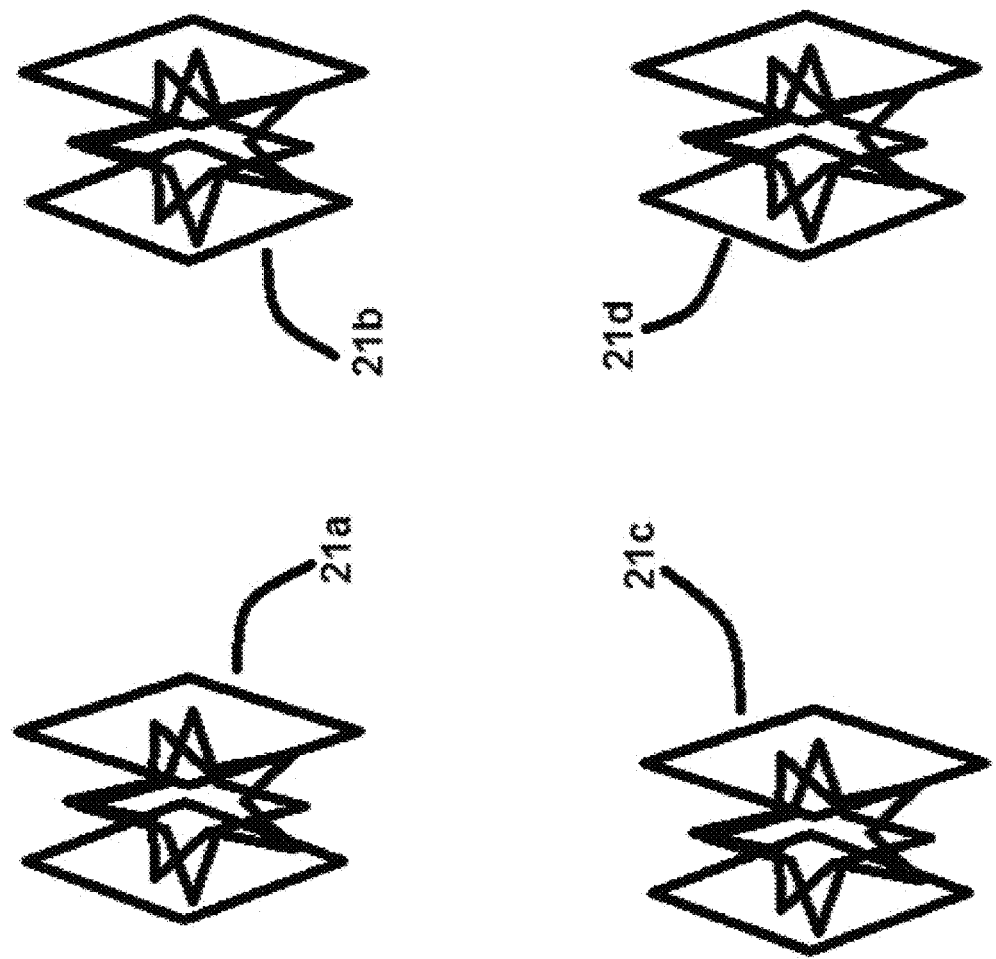
FIG. 3 is another embodiment of the present invention featuring crystal forms that may be utilized for authentication of operators, patients, animals, devices, machines and data segments, as well as conduits for transferring data.

Combining now FIG. 1 and FIG. 2, shown in FIG. 2 are 18a shows the aperture housing of the organic and artificial life form structure. In organic life forms 18a would represent a person's eye or cornea. Also shown is the cornea 20a, with an aperture, also known as the pupil 19a. The pupil may be interchangeably referred to in this invention as the iris. Depending on the source of light, level of excitement, a particular emotion or a preset dimeter (for inanimate embodiments) the pupil 19a is shown in an enlarged position. The shrinkage or enlargement of the pupil 19a may also be induced by the light emitter device 7. The cornea, or aperture 18b demonstrates when the light transmitter is lowering the light level transmitted to the eyeball 19b and aperture 19b decreasing the opening to the pupil 19a, which may be a camera aperture 1 or another optical component of an inanimate object 17. The system and method of allowing light levels to change may be achieved by an individual blinking eye lid 10, 14 of one or more eyeballs or camera lens cover apertures 24. Therefore, one of the ways the communication device 1 may authenticate an object, or at least ensure that the authentication is a true specimen and not an object of impersonation or falsification, is to attempt to induce a certain behavior from a pupil 19a and then measure its size, or to compare the size of the pupil 19a or an optical component 17 in reference to the level of lighting, or level of excitement, at that given moment.

The synchronization or a combination of various biological sensory responses authenticates the movement in the eyeball 5 and iris 4. The video of the movement pupil or iris 19a authenticates the alive status of the individual identifying them against comparison of stored data of the individual contained within the device. The device systems communication system 1, when used against an eye 5, or an inanimate object 5a provides true identification of the operator of the device by measuring both the identity of the object or person, by also determining whether the device or person is alive or active, and by determining if the object is real, meaning, responds to real time stimuli, such as changes in light intensity. This sensory result can then be used in unlocking a device or granting access to it, thus allowing operation of a device being thus authenticated.

Figure 4:
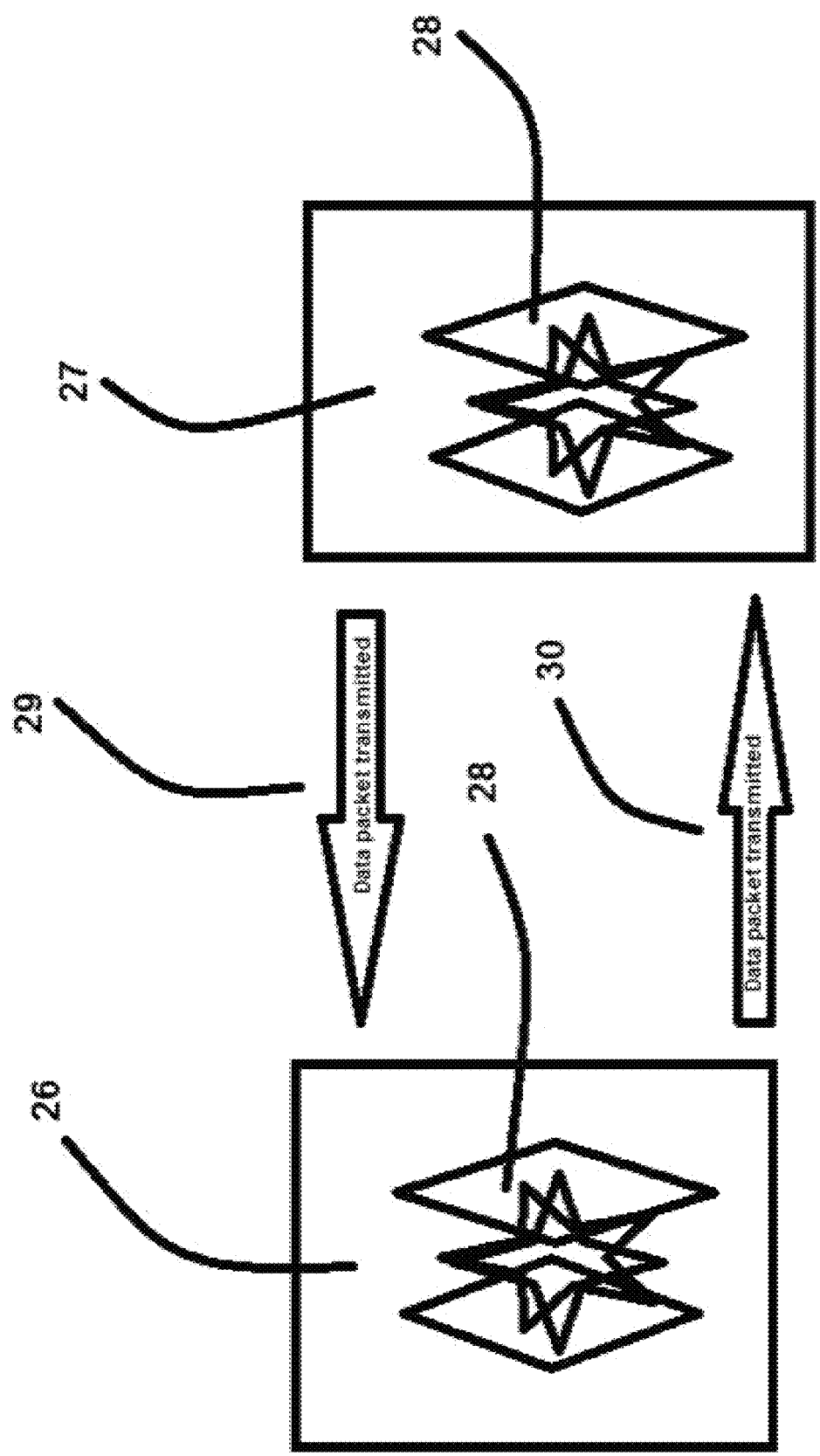
FIG. 4 is another demonstration of data transfer utilizing technological concepts described in FIG. 3.

Another embodiment of the present invention (FIG. 4) 26, 27 may be used as three dimensional (3D) communication data packet crystal 28 for sending and receiving information 29, 30. The data packets can be transmitted via transceiver 26 three dimensionally data crystal packet 28 to a three dimensional receiving reading unit 27. These data packets can be designed using the natural design of ice crystals formation. The data packets crystals 28 may use multiple colors indicating various bits of various data and information being communicated between transceivers of the data packet crystals. This new invention may use an all new three dimensional communicating code 28 technology as a "stand alone" system or it may use a combination of computer languages. The 3D system will allow for a much greater amount of data to be transmitted through the transceivers in a less amount of time and using much less bandwidth since unlike a serial binary data, the data stored in the crystal packet 28 may be transmitted completely, or in a series of fragments using a crystal packet 28 of a particular type. Once received, the reading unit 27 will then decode the data stored on the crystal packet 28 using a crystal reference guide or code stored locally, or in a readily accessible remote location.

Figure 5:
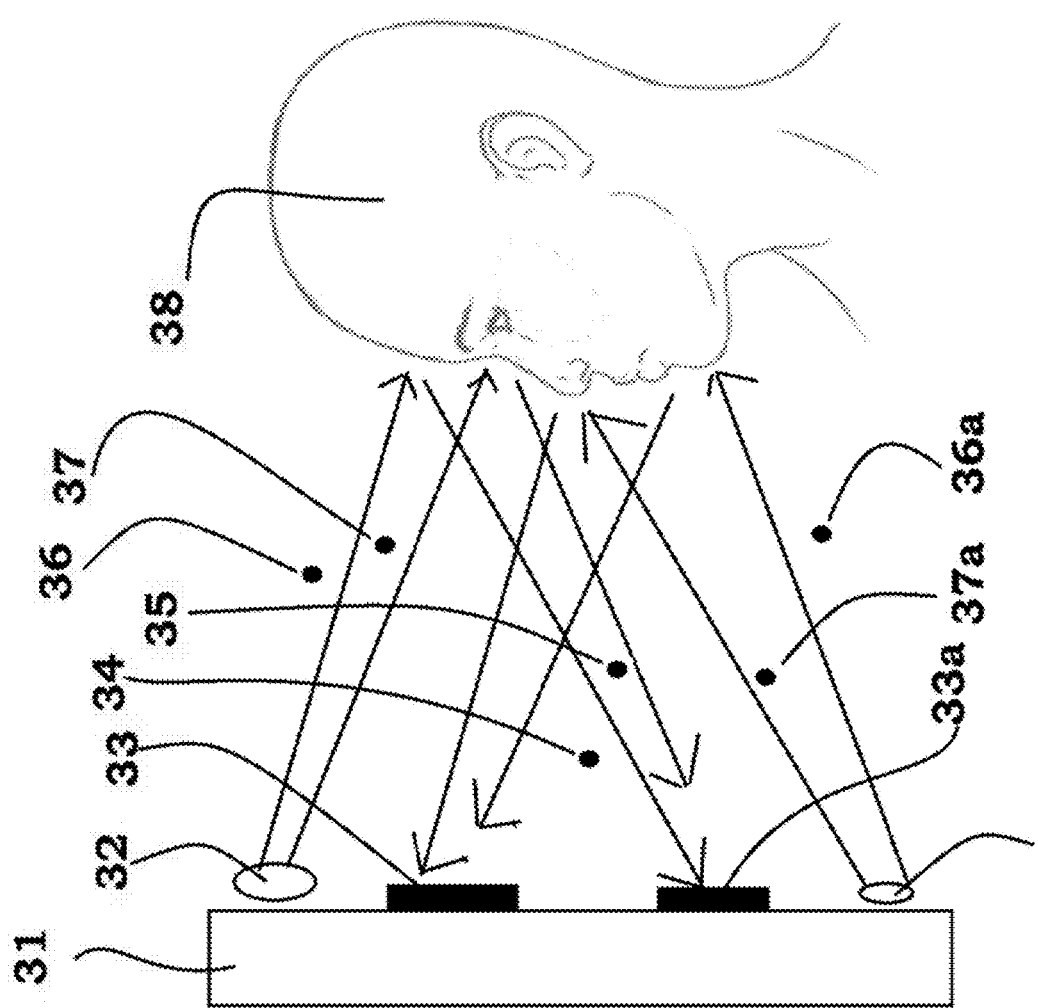
FIG. 5 is a diagram encompassing the processes described in FIG. 1 and FIG. 2.
Figure 6:
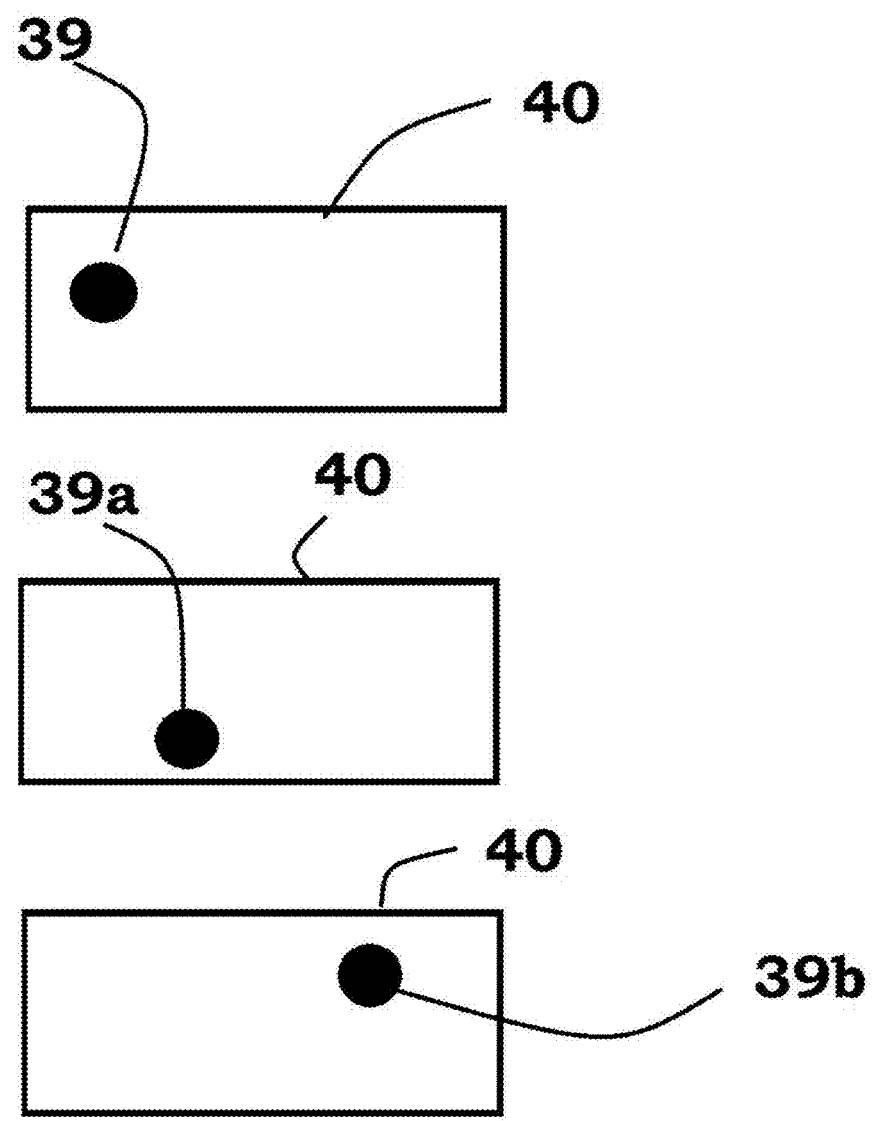
FIG. 6 is a diagram providing one authentication method that utilizes a subject's feedback to an external stimulus as a form of authentication.
Figure 7:
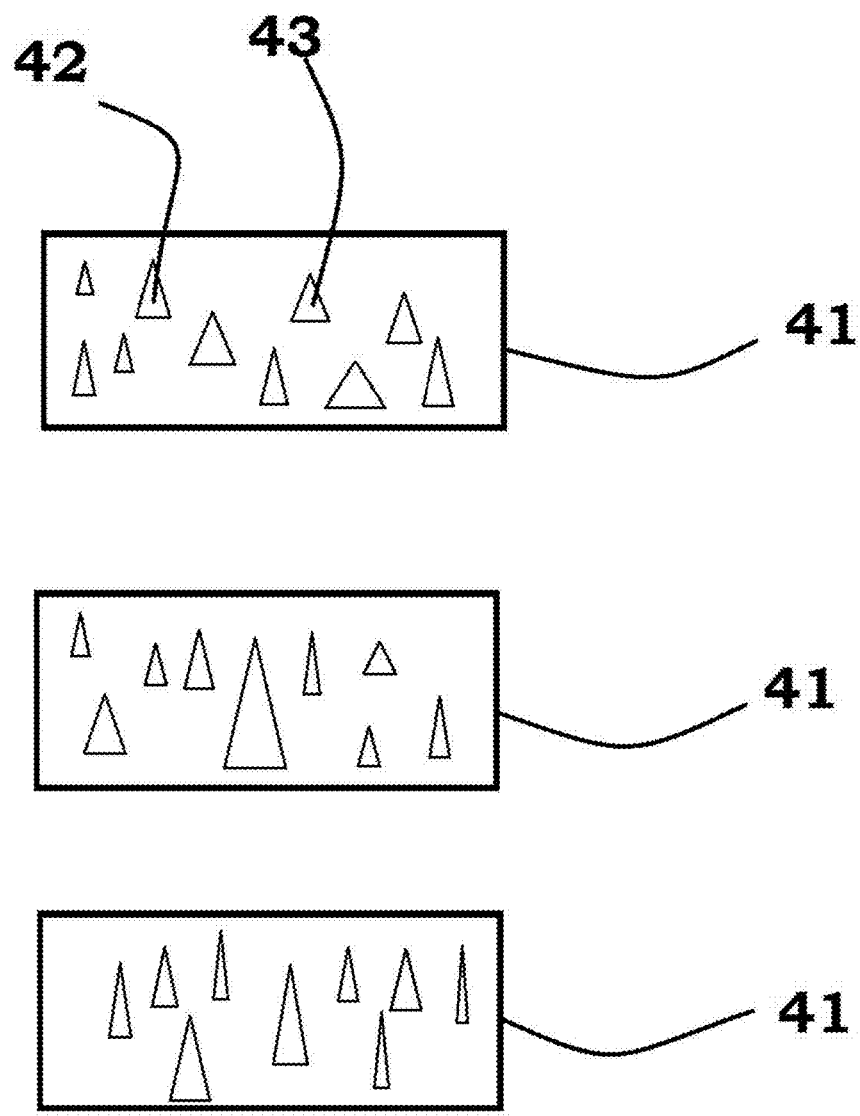
FIG. 7 is a diagram of another authentication method utilizing another stimulus response, namely, analysis of a reflection of visible light originating from a device disclosed in the present invention.
Figure 8:
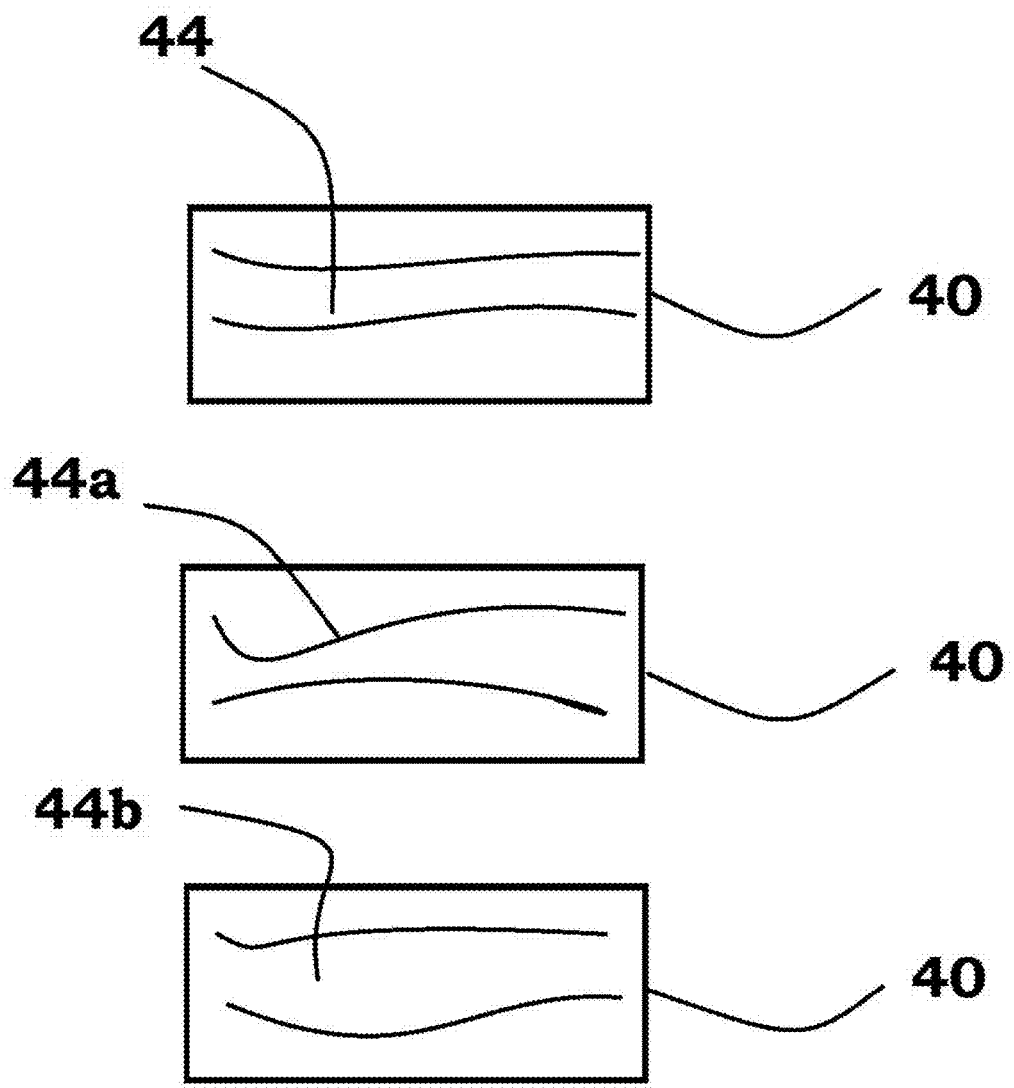
FIG. 8 is a similar concept to FIG. 7, but utilizing waive patterns instead of the tear drops, or waves instead of strobes.

Another embodiment of the present invention shown in FIG. 5 incorporates several authentication systems already described in previous figures. Using the combination communication device 31, signals transmitters and readers may be used to authenticate an object or acknowledge the health condition, alive status and identification of an operator/patient, otherwise referred to as an object. The system operator activates a combination communication device 31 and/or devices which then activates an array of sensors, such as the light emitting device 33, or a sound emitting device 33a. The light and sound emitting devices 32 and 32a may be combined. The light and sound emitting devices 32 and 32a may be coupled in a series and directed at the same object 38, to determine volume, or to draw a detailed image of a face belonging to object 38. The face can then be used to match to an authorized faced, or to detect whether a face is displaying a grimace or an expression indicating a particular emotion or distress.

Still referring to FIG. 5, the combination device 31 may also have sensors 33 and 33a that may carry out various functions or combination of functions, such as echo locators, light sensors, motion, and infrared sensors. Sensors 33 and 33a may be a combination of sensors, containing all those already mentioned in the previous sentence and coupled with microphones, sound distribution system (external and internal). A combination sensor is ideal for small or micro-embodiments of the same invention.

Figure 9:
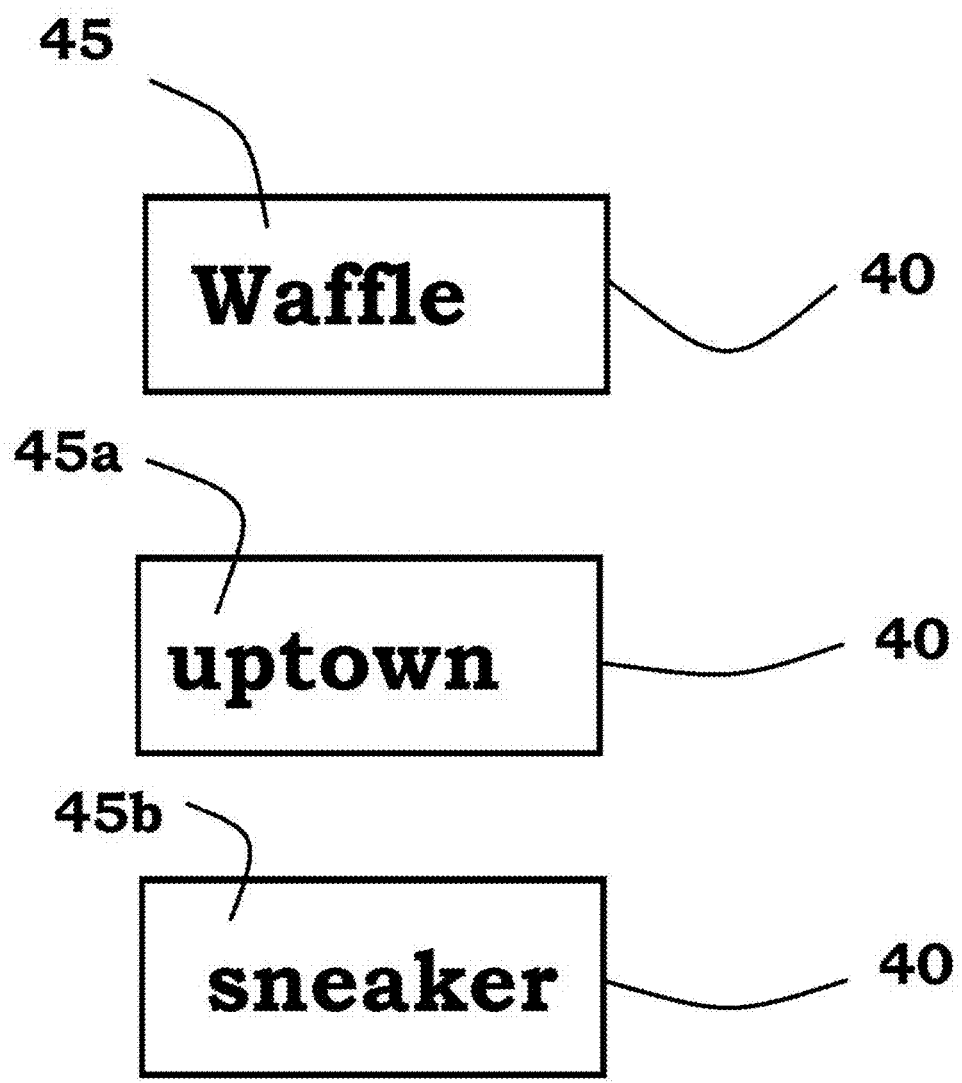
FIG. 9 is another concept disclosed in FIGS. 7 and 8, this time a subject is prompted to respond to visible commands, and is measured for accuracy, voice authentication or voice pitch analysis.

Shown in FIGS. 6-9 are various optical or visual screens that may be displayed to an object, where the commination device 1 or the combined communication device 31 may then monitor the response, to determine identity or health status of the object being monitored. For example, screen 40 displays waves of light. The aperture or pupil 19a naturally or even involuntarily tracks these lines. Furthermore, the light from the line screen 40 or the teardrop screen 41 forces a reflection of a certain type from the object being monitored (such as natural and artificial eyes S and 5a). In FIG. 9 the object is forced to read a statement. The combined sensor 33 and 33a will then be able to detect the voice, and match the voice to the object, or detect a pitch of the voice, slurring of speech, etc. Additional outside stimuli that produce detectable responses include, but are not limited to visual apparatuses, scent emitters, vibration apparatuses, all levels of light spectrum emitting devices, electronic needles and pressure distributions panels (medication delivery and acupuncture/acupressure electro impulse emitters and brain analyzing sensors.

The communication devices 1 and 31 may be easily extended to more therapeutic purposes. For example, the combined sensors 33 and 33 may be used to detect a physical condition or a physical infirmity, and automatically determine whether intervention is required. Intervention may then be accomplished by already known means, such as medication dispensing, summoning of emergency help, remote activation or adjustment of embedded artificial organs, conduits and monitors. The present invention may be applied within the context of diabetic monitoring and treatment.

Location, authentication and monitoring may be achieved using the infinite spectrum of sounds produced from sound producing devices such as 7, 32 and 32a. An array of sounds directed from multiple angles, such as from 32 and 32a simultaneously, will paint an accurate picture of the object and object's surroundings and secondary or indirect factors. Such as, monitoring the object directly, but also be able to detect external presence of others or other things. Resulting from this, the sensors 33 and 33a will then be able to detect responses to stimuli from the device 31 and responses from stimuli that are not produced by the device 31.

The sensors 33, 33a, and the camera device 2 may also detect impulses from external signal device(s) i.e. camera(s), thermal camera(s), microphone, light absorbent material, laser light transceiver, LED or alike. Pupil (FIG. 1) 4 (FIG. 2) 19a, 19b (FIG. 5) 33, 33a expansion and contraction when synchronized with light impulses authenticates the operator as being alive and in real time various health checks. The operator's iris is then set in motion (FIG. 1) 7 (FIG. 5) 32, 32a by the random light pulses aimed at the operator's eyes, pupil, irises and facial features. A retina and/or iris scan is used in conjunction with the "Alive Iris" checking system proving identity of the operator and health condition of (FIG. 5) 38 operator/patient/animal/machine. This system may incorporate a (FIG. 5) 32, 32a pulsating laser for long distance authentication and identification purposes of an operator.

Figure 10:
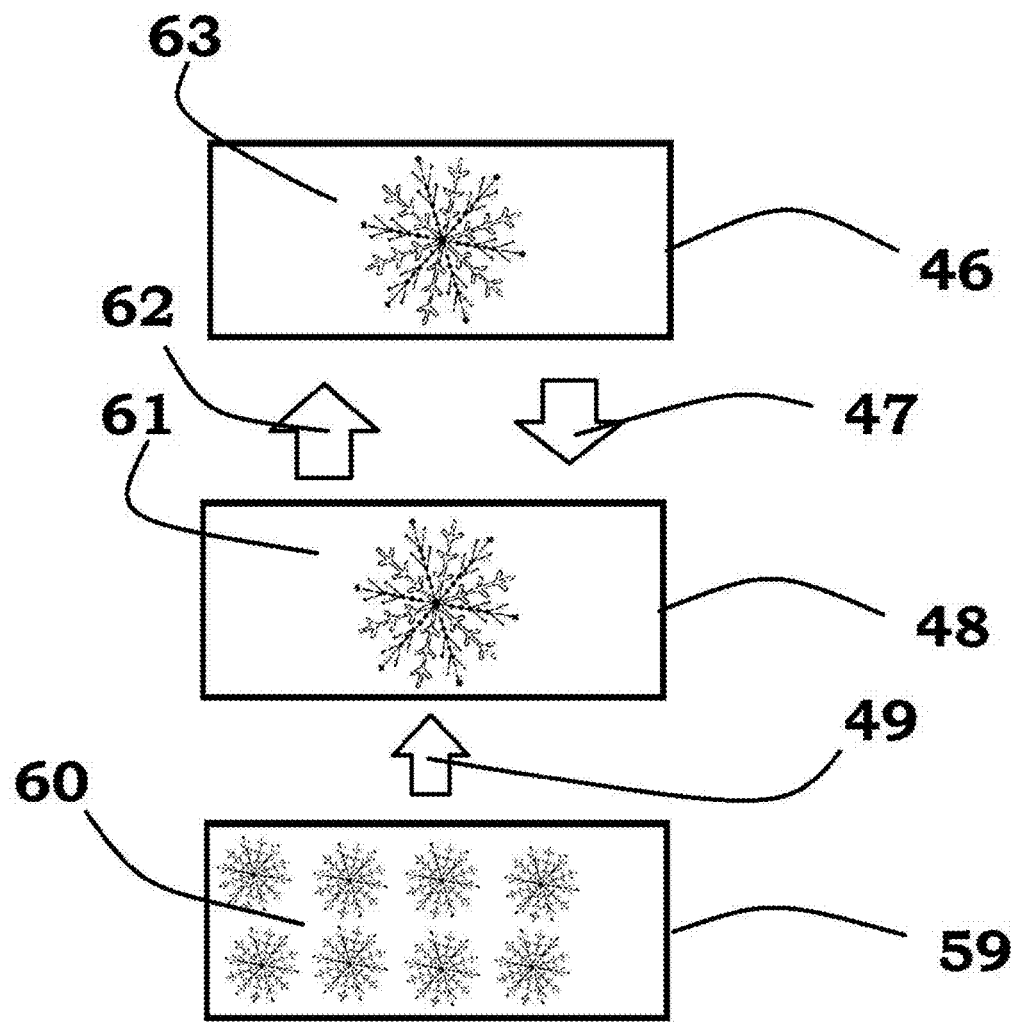
FIG. 10 is another embodiment of authentication concepts utilizing crystal technologies, namely, firewall FIGS. 11 and 12 demonstrate further attributes and merits of a crystal based authentication and data transmission technologies.
Figure 11:
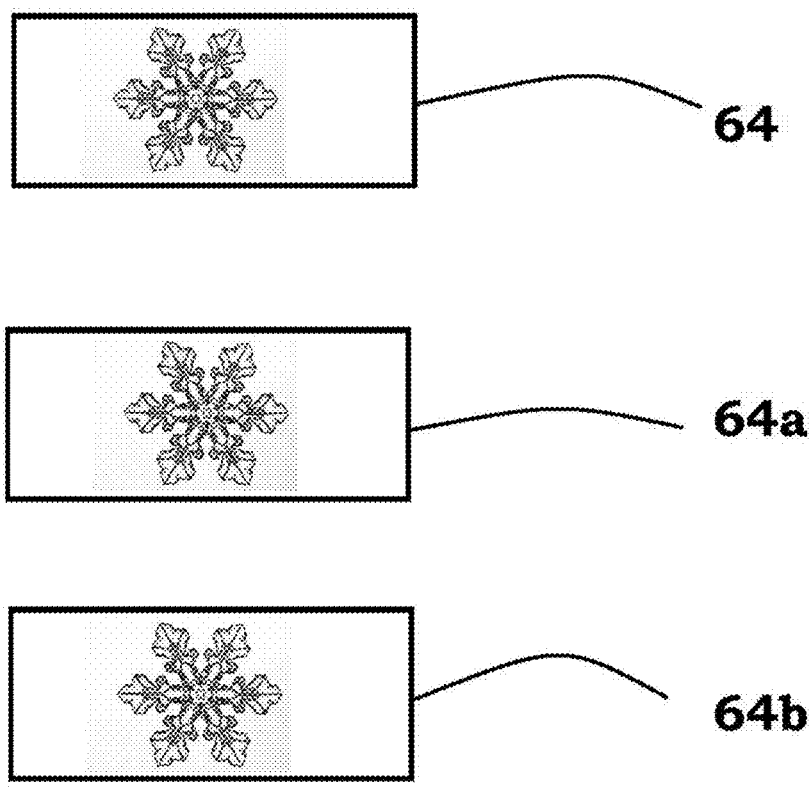

When this system is in use, the camera acknowledges the activities of the objects in the background to make a determination of the activities against the movements of the operator's iris 19a or (FIG. 1) 24 aperture of an artificial operator or eye. The device may contain an individually designed (FIG. 1) 22f crystal for device identification purposes. The design of the crystal may follow a frozen water crystal in the form of a snowflake (FIG. 1) 22f (FIG. 11) 64, 64a, 64b configuration. This will provide machines, humans and animals with an individual crystal (biometric) identity. There may be one, two or more of the crystals made for individualized communications between the crystals for security purposes. This communication technique will allow for the manufacturers of the devices to have encrypted and restricted communications (FIG. 10) 61, 63 between the device crystal firewall security platforms on servers and machines.

Alive Biometric Signatures will create a simplistic accurate vetting and monitoring of individuals eliminating terrorists & terrorism. Alive Biometric Signatures secures internet portals, data servers, switching hubs and all communication devices eliminating cyber warfare & hacking.

Alive Pupil Tracker system may produce a strobe light through light producing devices 7, 32 or 32a. The "Alive Iris" systems identifies individuals at high accuracy rate while delivering a series of health status reports. The system provides analyzation "live", "in real time" truth and lie detection depending on the dilation or reduction of the pupil 19a, 19b based on external stimuli. This present invention (FIG. 1) 1, 2, (FIG. 2) 19a, 19b (FIG. 5) 31, 32, 32a, 33, 33a analyzes the eye, pupil, iris, retina, eye lids, curvature of lens, eye, eye socket and surrounding area of skin for graying, bumps, and various other abnormal skin conditions. "Alive Iris/Pupil/Retina" can determine the following: Fear, anger, pain, love, drugs, alcohol, & lying from analyzing alterations in pupil size. Skin Cancer, Cloudy Eye, Myasthenia Gravis, HIV/AIDS, Heart Attack, Stroke, Exophthalmos, Arcus Senilis, Homer's Syndrome, High blood pressure, Marfan's Syndrome, Hypertension, Head injuries, Metastatic cancer, Diabetes, Autoimmune disorders, High cholesterol, High triglycerides (FIG. 1) 1, 2, (FIG. 2) 19a, 19b (FIG. 5) 31, 32, 32a, 33, 33a all can be determined by the eye and surrounding area.

Another embodiment of the present invention (FIG. 5) 36, 37, 37a, 37b uses subsonic sound impulses produced by devices 36, 37 and 37a and 37b, with laser light impulses directed at the features of the operator/patient/animal/machine providing (3-D) images of the contours once these have been interpreted by sensors 33, 33a, 34, 35, thus painting a three dimensional object.

(FIG. 6) 39, 39a, 39b incorporates a bouncing object to be followed by the eye and tracked by the eye tracker device.

(FIG. 7) 42, 43 incorporates a random light emitter to be reflected in the eye lens and tracked by the reflector tracker device. (FIG. 7) 42, 43 show sparklers of light sequences utilizing various light levels and colors similar to light being reflected on water.

(FIG. 8) 44, 44a, 44b demonstrates various light patterns for creating health modification systems.

(FIG. 9) 45, 45a, 45b demonstrates the use of a random word emitter to be tracked by sound receiver sensors and mouth movement tracking software.

(FIG. 10) 60, 61, 63 shows one example of a crystal firewall encryption design. (FIG. 10) 48 is manufactures crystal firewall encryption system where 46 shows end user's machine crystal firewall encryption transceiver device.

Figure 12:
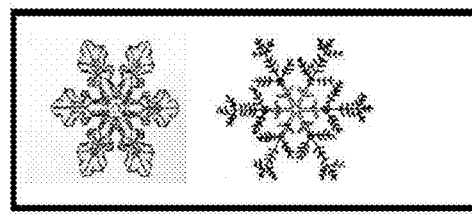
Figure 12:
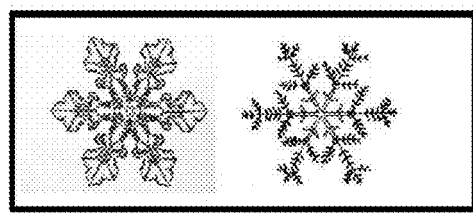
Figure 12:
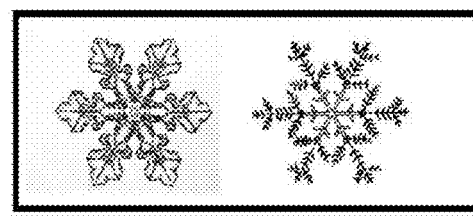

(FIG. 11) 64 top view, 64a side view and 64b front view of the three dimensional identification encrypted code and data packet (FIG. 12) 64c top view, 64e side view, 64e front view transferring systems. The crystal data packets use an array of colors combined with segments of information stored on pinnacles incorporated into the crystal formations. Crystals (FIG. 12) 64c, 64d, 64e have multiple purposes from identification of humans, animals, artificial devices, communication, data transmission, life record of information and data transfer. Crystals record every event in real time of an operator/patient/animal/machine throughout the life of the operator/patient/animal/machine. Data from crystal(s) is then transferred to receptacle for collecting data from the crystal(s) for the storage of data preferably in a vault.

Figure 13:
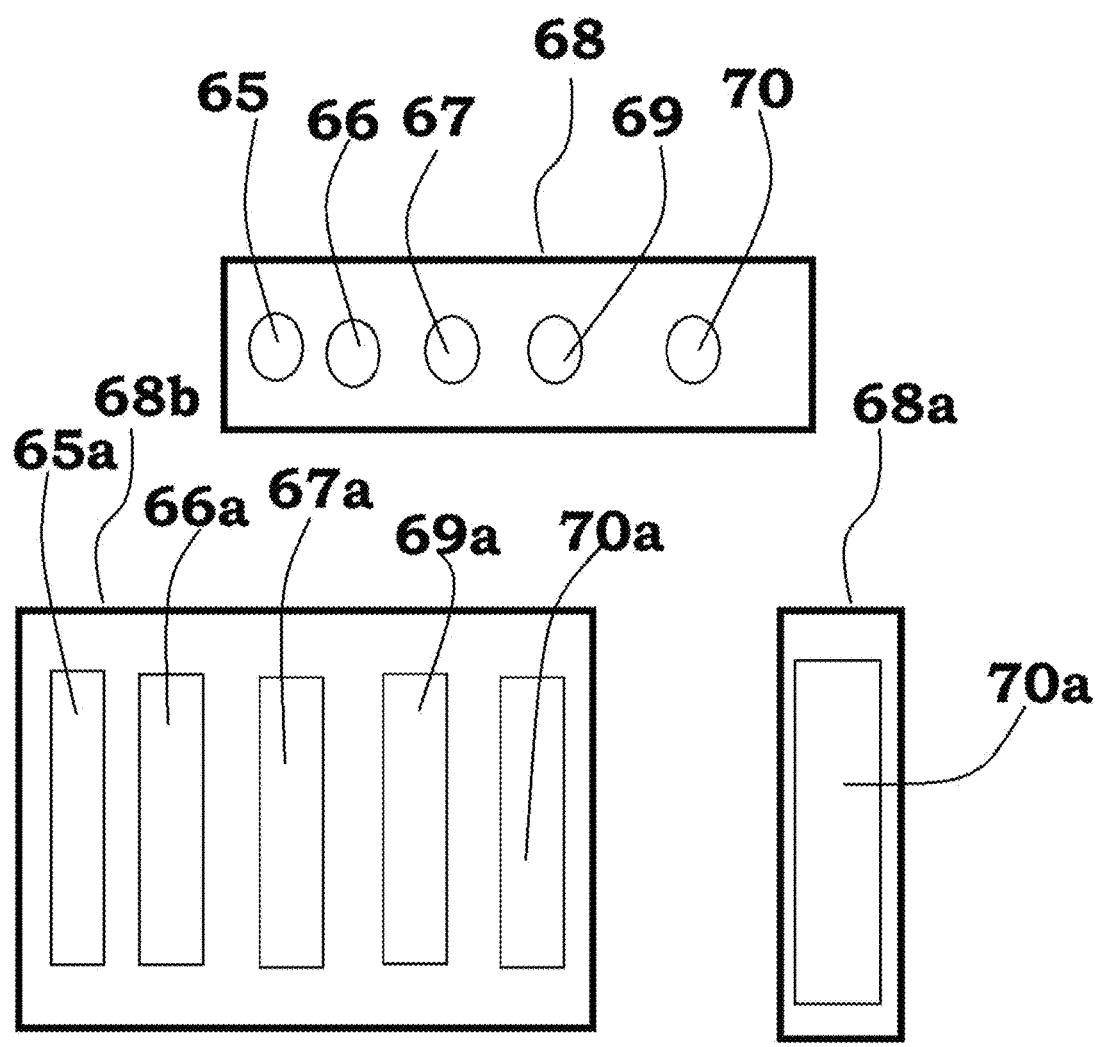
FIG. 13 is diagram illustrating a scent producing device required to enable authentication methodologies utilizing scents.

Another embodiment of the present invention is a scent sensory sensor system for receiving natural scents as well artificial scents and odors. (FIG. 13) 68 is a scent storage device utilizing numerous natural and artificial scents stored in numerous scent canisters 65, 66, 67, 69 70 for the manufacturing of an infinite number of scents and odors. Canisters may contain other materials like gases and solids for the creation of solids or gasses for building crystal codes for use in scent sensory sensor systems. (FIG. 13) 68a is side view of cartridge, 68a is front view of scent canister cartridge. Scent sensory system can be connected to any device.

Figure 14:
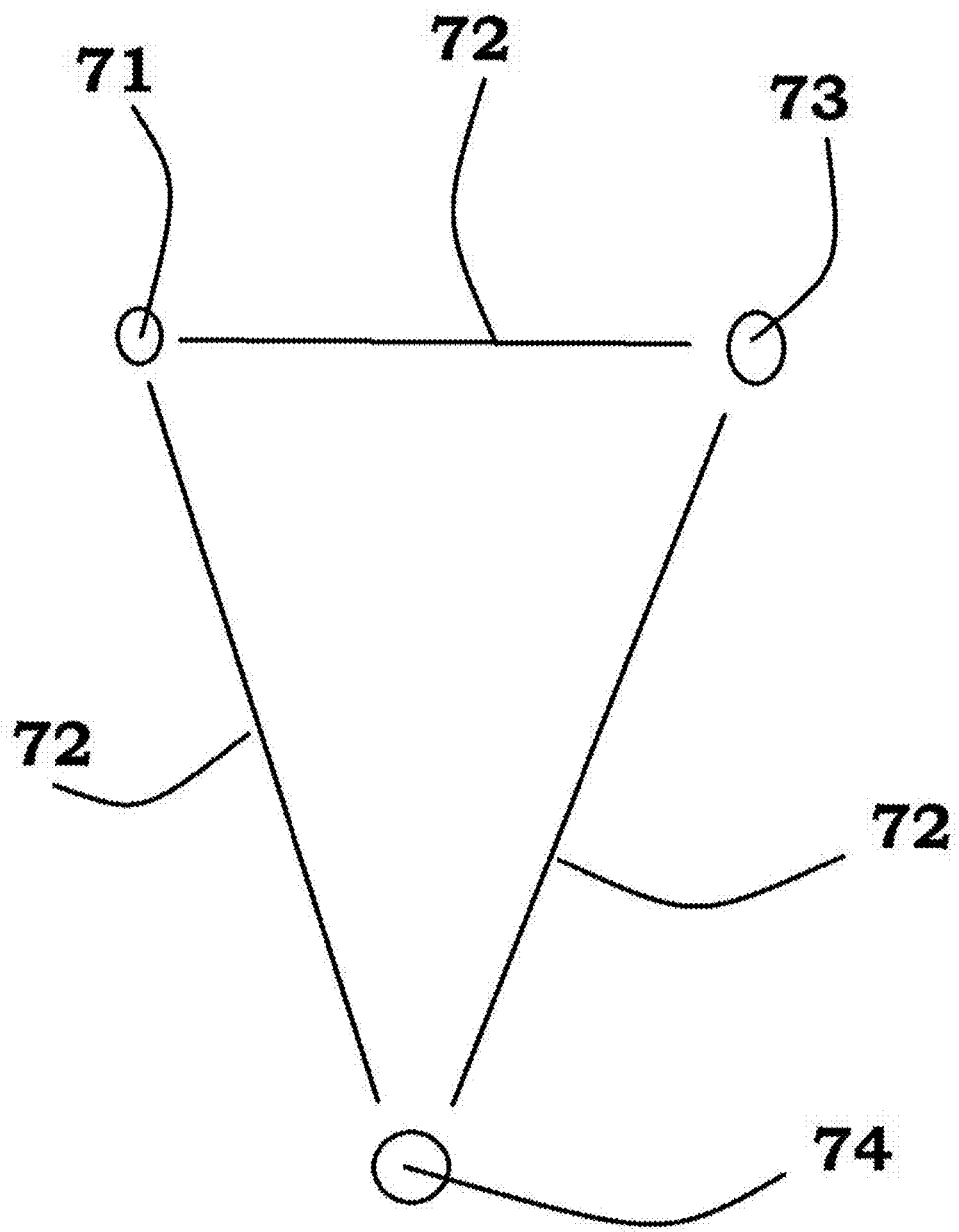
FIG. 14 merges the technologies of FIG. 1 and crystal authentication technologies.

Another embodiment of the present invention is a laser light communication system. The system uses encrypted crystal code sent and received with light emitters infused with light detectors capturing three dimensional images of the crystal codes. The codes are sent via light emitters for sending impulses of photons at the receiving sensor which then gets deciphered and formatted for data retrieval. In (FIG. 14) 71, 73, and 74 are three devices sending and receiving data utilizing 72 the encrypted crystal code sent via light waves and impulses.

Figure 15:
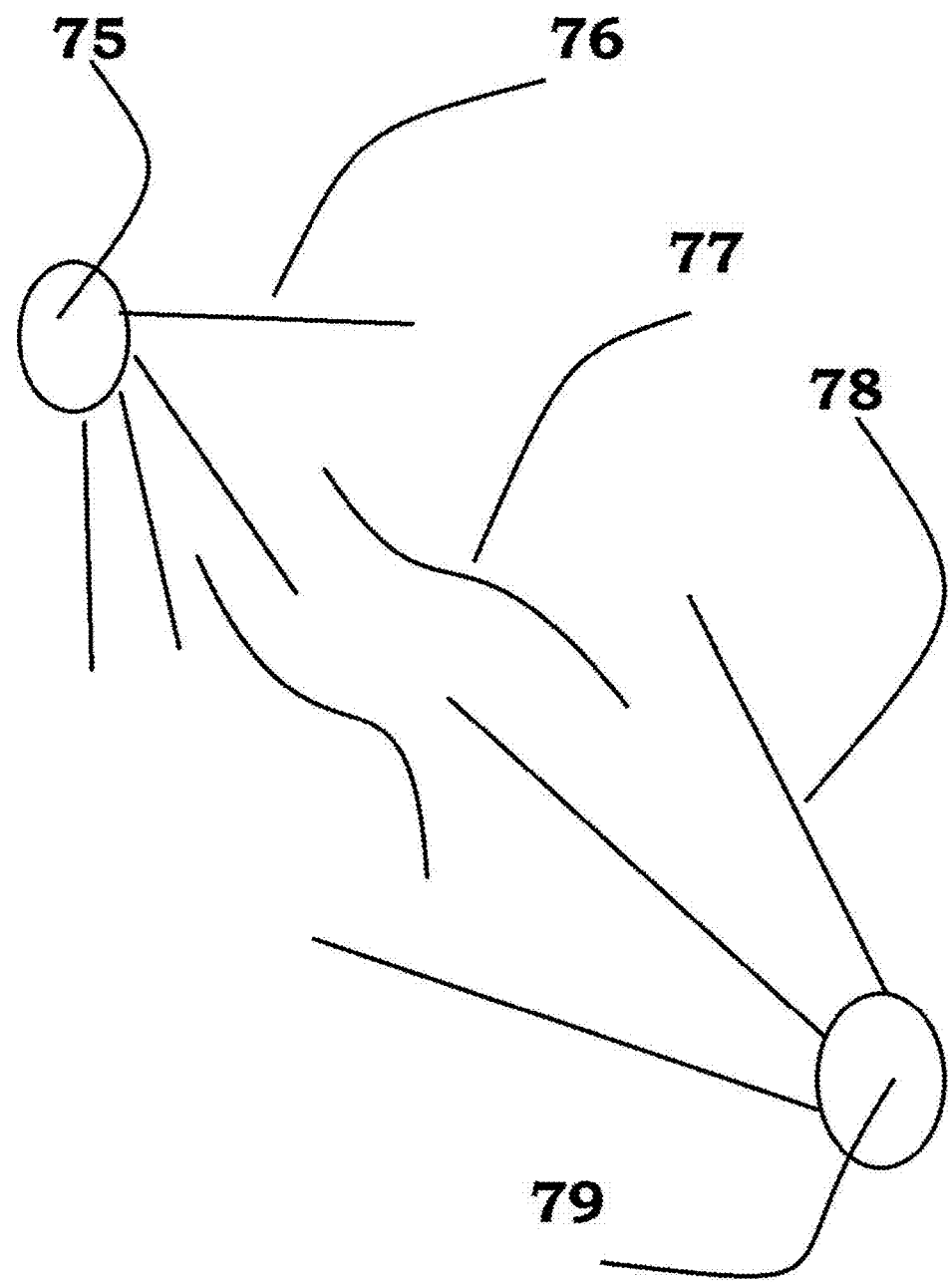
FIG. 15 is a demonstration of one application of scent technology where a scent producer (sender device) transmits a scent cocktail for authentication by a scent reader.

Another feature to the present technologies is a scent sensory sensor systems shown (FIG. 15) 75, 79 are two devices in action. Both devices 75, 79 are manufacturing and reading scents. Scents can interconnect from more than one device which then can lead to creating additional 77 scent for further development of the technologies.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed:

1. An apparatus comprising a system with an array of sensors, sound and light emitting and receiving devices having at least one object control from a monitored object comprised of an operator, a patient, an animal, or machine, control of at least one performance parameter of the system; at least one iris/retina biometric sensor; at least one physiological iris/pupil sensor; at least one infinite random light emitter; said at least one iris/pupil biometric sensor; said at least one physiological pupil sensor and said one infinite random light emitter operatively connected and synchronized communication with each other utilizing at least one central processing unit; said at least one biometric sensor and said at least one physiological sensor delivering a parallel array of sensory readings to said central processing unit; said central processing unit capable of detecting a normal or an abnormal sensory reading; said at least one central processing unit capable of effecting said at least one performance parameter in response to said sensory reading; and said central processing unit recording said sensory reading on a storage medium to be used for identifying and detection of said alive status and health condition of the monitored object in real time.

2. The apparatus of claim 1, further comprising sound emitting device; sound receiving device; for said identification; of said monitored object, Sound emitting device emits various sounds and echoes at the monitored object for detection of direction of sounds waves bouncing; echoing off the subject, Sound direction detection device receives sounds; sound pattern determines shape of object; then said device creates a 3-Dimensional image of the subject matter.

3. The apparatus of claim 1, further comprising light emitting device; light receiving device; for said identification; of monitored object, Light emitting device emits various light waves at the monitored object for detection of direction of light patterns bouncing off the monitored object; wherein light direction detection device(s) receives light patterns; light patterns determine shape of object; then said device creates a 3-Dimensional image of the subject.

4. The apparatus of claim 1, further comprising scent sensory sensor system comprising; said at least one manufacturing device; said at least one scent receiving device; said at least one scent emitting device for said identification; of the monitored object, wherein scent manufacturing and emitting device emits various scents for identification and authentication of at least one said monitored object.

5. The apparatus of claim 1, further comprising; thermal receiving device; for said identification; of said monitored objecting said at least one device detecting; heat signature from a source comprising eyes, epidermis, mouth, breath or any combination thereof.

6. The apparatus of claim 1, further comprising visual emitting device; speech recognition receiving device and system; for said verification of said visual effect or word; created by said monitored object, Visual emitting device emits various visual effects; at said at least one monitored object for detection of visual effects/words to be spoken by at least one operator/patient/animal/machine; said at least one mouth movement analyzer; it is said at least one sensor recognizing; at least one mouth; said at least one movement of mouth detector then responds as normal or abnormal sensory reading distributed by the infinite word randomizer displayed to induce a response by said monitored object.

7. The apparatus of claim 2, wherein said operative coupling of said at least one iris/retina biometric sensor; said at least one pupil physiological sensor; at least one light emitting device are in synchronized coordination.

8. The apparatus of claim 1, wherein said operator control is continuous.

9. The apparatus of claim 1, wherein said at least one iris/retina biometric sensor or said at least pupil physiological sensor are capable of monitoring external stimuli impacting an operator performance.

10. The apparatus of claim 1, wherein said at least one physiological sensor or said one biometric sensor is infrared.

11. The apparatus of claim 1, wherein said at least one communication crystal sensor reading receiver device or said at least one crystal code communicator emitter is sent through; at least one laser beam transceiver.

12. The apparatus of claim 1, wherein said at least one identification crystal code symbol; at least one duplicate identification crystal code symbol communicates; with said identical twin symbol as encrypted firewall.

13. The apparatus of claim 12, wherein said at least one crystal code symbol is encrypted data packet and said crystal code symbols are used to compress binary code into said crystal code data packet.

14. The apparatus of claim 12, wherein said at least one crystal code symbol uses color coded segments and said at least one colored coded segment is a data repository vault.

15. The apparatus of claim 1, wherein said at least one acupressure device is activated by said communication device or said at least one is an article of clothing.

16. The apparatus of claim 1, wherein said at least one acupuncture device is activated by said communication device or said at least one is an article of clothing.

17. The apparatus of claim 1, wherein said at least one vibration device is activated by said communication device; it is said at least one is an article of clothing.

18. The apparatus of claim 1, wherein said pupil dimension tracking sensory systems is used for determining truth or lie.

19. The apparatus of claim 1, wherein said pupil dimension tracking sensory systems is used for determining brain operations and injuries.

20. The apparatus of claim 1, wherein said pupil dimension tracking sensory systems; said at least one retina scanner sensor; it is said at least one camera is used for determining health conditions and status of temperament such as: Fear, anger, pain, love, drugs, alcohol from analyzing alterations in pupil size, Skin Cancer, Cloudy Eye, Myasthenia Gravis, HIV/AIDS, Heart Attack, Stroke, Exophthalmos, Arcus Senilis, Homer's Syndrome, High blood pressure, Marfan's Syndrome, Hypertension, Head injuries, Metastatic cancer, Diabetes, Autoimmune disorders, High cholesterol, High triglycerides all can be determined by the eye and surrounding area by means of sensors; camera, infrared camera, movement speed of iris/pupil opening, software comparison analyzation system, remote physician analyzation.

* * * * *